(12) United States Patent
Esten

(10) Patent No.: US 6,427,883 B1
(45) Date of Patent: Aug. 6, 2002

(54) GLOVE DONNING AND DOFFING ARRANGEMENT

(75) Inventor: Noel Kendall Esten, El Sequndo, CA (US)

(73) Assignee: Jan Perry Esten, Divide, CO (US)

( * ) Notice: Subject to any disclaimer, the term of this patent is extended or adjusted under 35 U.S.C. 154(b) by 0 days.

(21) Appl. No.: 09/798,358

(22) Filed: Mar. 2, 2001

(51) Int. Cl.[7] .............................................. A47G 25/80
(52) U.S. Cl. ...................................................... 223/111
(58) Field of Search ................................ 223/111, 112, 223/1, 120; 2/154, 160

(56) References Cited

U.S. PATENT DOCUMENTS

| | | | |
|---|---|---|---|
| 4,876,747 A | * 10/1989 | Coffey et al. ................... | 2/168 |
| 4,915,272 A | * 4/1990 | Vlock .......................... | 223/111 |
| 5,345,368 A | * 9/1994 | Huff ............................ | 362/103 |
| 5,706,521 A | * 1/1998 | Haney ............................ | 2/160 |
| 5,749,098 A | * 5/1998 | Evans ............................ | 2/123 |
| 5,868,290 A | * 2/1999 | Green, Sr. et al. ........... | 223/111 |
| 6,021,935 A | * 2/2000 | Yonezawa ................... | 223/111 |

* cited by examiner

Primary Examiner—Bibhu Mohanty
(74) Attorney, Agent, or Firm—Raymond Y. Chan; David and Raymond Patent Group (57) ABSTRACT

A glove donning and doffing arrangement includes at least a glove, at least a glove station for supporting the glove in a hand-down position, a first attaching element provided on a non-operating area of the glove, and a second attaching element provided on the glove station in such a manner the glove is adapted to detachably attach on the glove station in a hand-down position by attaching the first attaching element to the second attaching element. Therefore, in the hand-down position, a wearer is capable of donning and doffing the glove easily while the wearer's hand is in naturally hang-down manner without contacting the exterior surface of the glove.

14 Claims, 7 Drawing Sheets

GLOVE DONNING AND DOFFING ARRANGEMENT

BACKGROUND OF THE PRESENT INVENTION

1. Field of Invention

The present invention relates to gloves, and more particularly to a glove donning and doffing arrangement, wherein each glove is held in a hand-down position, so as to facilitate a wearer to wear and remove without skin contacting with an exterior surface of the glove, and thus the wearer's skin is prevented from contacting with chemical stained on the glove.

2. Description of Related Arts

Gloves are used for not only keeping our hands warm but also protecting our hands so as to provide a sanitary condition of our hands. For example, in chemical industries, people wear gloves for preventing chemicals from contacting with their hands. It is extremely important that since some chemicals are hazardous, that may cause skin disease or even cancer. So, when people deal with the chemicals, they must wear gloves for protection.

However, such people may still have a chance to have skin contact with the chemicals while they remove their hands from the gloves and wear the used gloves on their hands. For example, it is not hassle that when a wearer removes his left glove from his left hand since his right hand still has the right glove thereon. However, after removing the left glove, his bare left hand must contact with the right glove in order to remove the right glove from his right hand in such a manner that his right hand may merely contact with the chemicals strained on left glove.

Moreover, when wearing the gloves, the wearer must use his bare hands to hold the gloves such that the wearer may merely touch the gloves with his bare hand in such a manner that the wearer's hands will contact the residual chemicals on the gloves.

U.S. Pat. No. 5,864,885, owned by Grinberg, discloses a glove A having an attaching loop A1 is suspendedly hanged on a hook A2 of the glove stand A3, as shown in FIG. 1A. However, the attaching loop A1 is affixed to an edge of the glove such that the wearer may have difficulty to remove the glove. Thus, the wearer also has no way to wear the glove without contacting with the glove surface in such a suspending position. So, the wearer may merely use his hand to wear and remove the glove as well.

Referring to FIG. 1B, U.S. Pat. No. 6,010,044, owned by Hsiao, discloses a sport glove B1 that is supported on a glove stand B2 in a hand-up position. In such hand-up position, the glove B1 may easier be worn and removed from the wearer. However, while the glove B1 is mounted on the glove stand B2, due to the gravity, the chemicals will drop down from the glove B1 to the wearer's arm. Moreover, it is quite difficult and troublesome to insert the support bars B3 into the gloves B1.

Therefore, there is no such an assembly in market available that the wearer does not require another hand to operate the donning and doffing process, so as to prevent the skin from contacting with the glove surface.

SUMMARY OF THE PRESENT INVENTION

A main object of the present invention is to provide a glove donning and doffing arrangement, wherein the glove is supported on the glove station in a hand-down position, which is facilitated for a wearer to wear and remove the glove.

Another object of the present invention is to provide a glove donning and doffing arrangement, wherein during the donning and doffing operations, the glove station can hold the glove in position so as to prevent the wearer's skin from contacting with an exterior surface of the glove.

Another object of the present invention is to provide a glove donning and doffing arrangement, wherein a holding member is affixed on a non-operating area of the glove, that does not interfere the normal operation of the glove.

Another object of the present invention is to provide a glove donning and doffing arrangement, wherein the hand-down position of the glove enhance the liquid such as chemicals automatically dropping down from the exterior surface of the glove by gravity.

Accordingly, in order to accomplish the above objects, the present invention provides a glove donning and doffing arrangement, comprising at least a glove, at least a glove station for supporting the glove in a hand-down position, and an attaching means for detachably mounting the glove on the glove station in the hand-down position, whereby, the glove is adapted for easily being worn and detached from a wearer's hand while the glove is supported on the glove station in the hand-down position.

DETAILED DESCRIPTION OF THE PREFERRED EMBODIMENT

Figure 2:
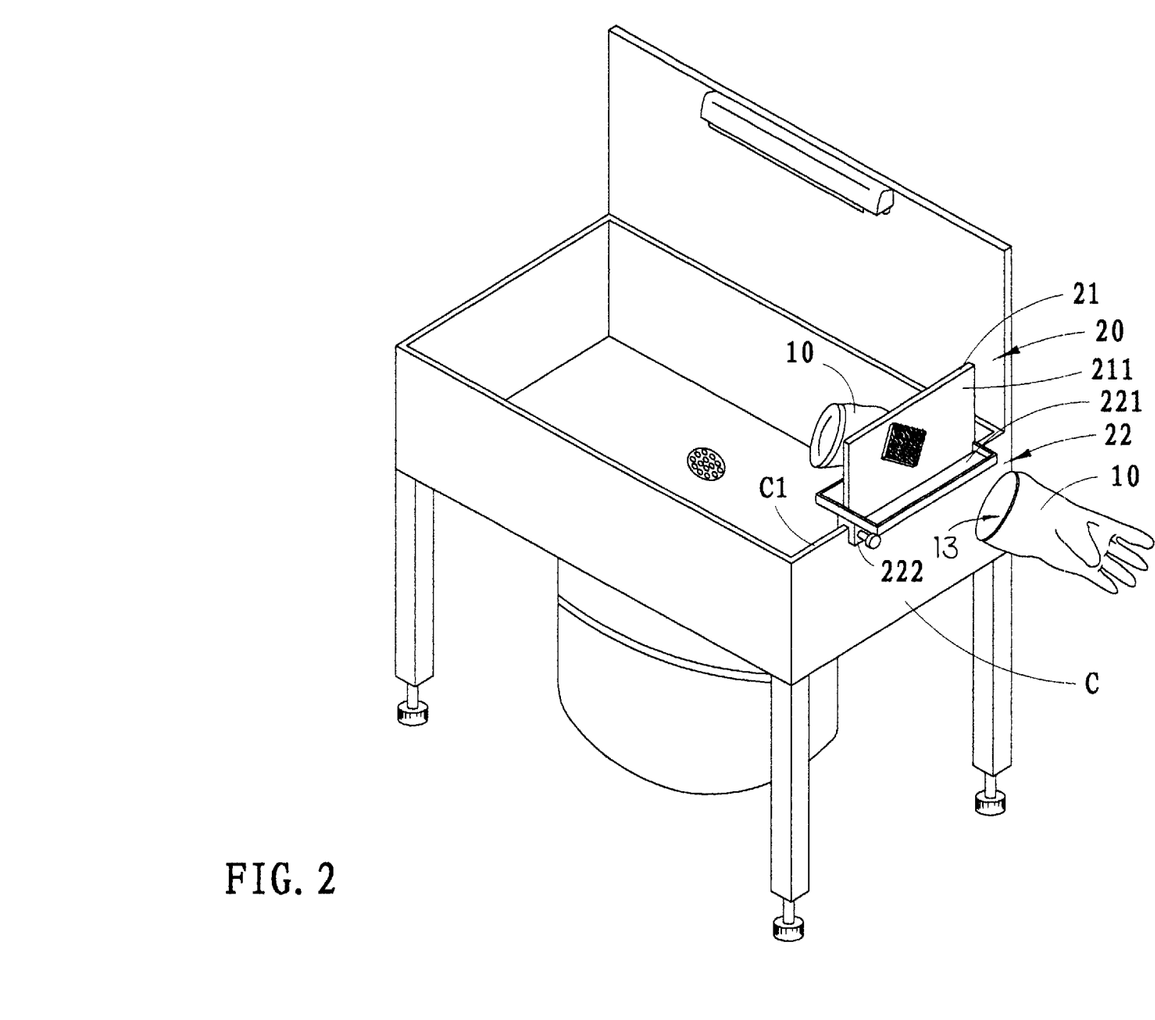
FIG. 2 is a perspective view illustrating how a glove donning and doffing arrangement of the present invention incorporated with a chemical wash table.
Figure 3:
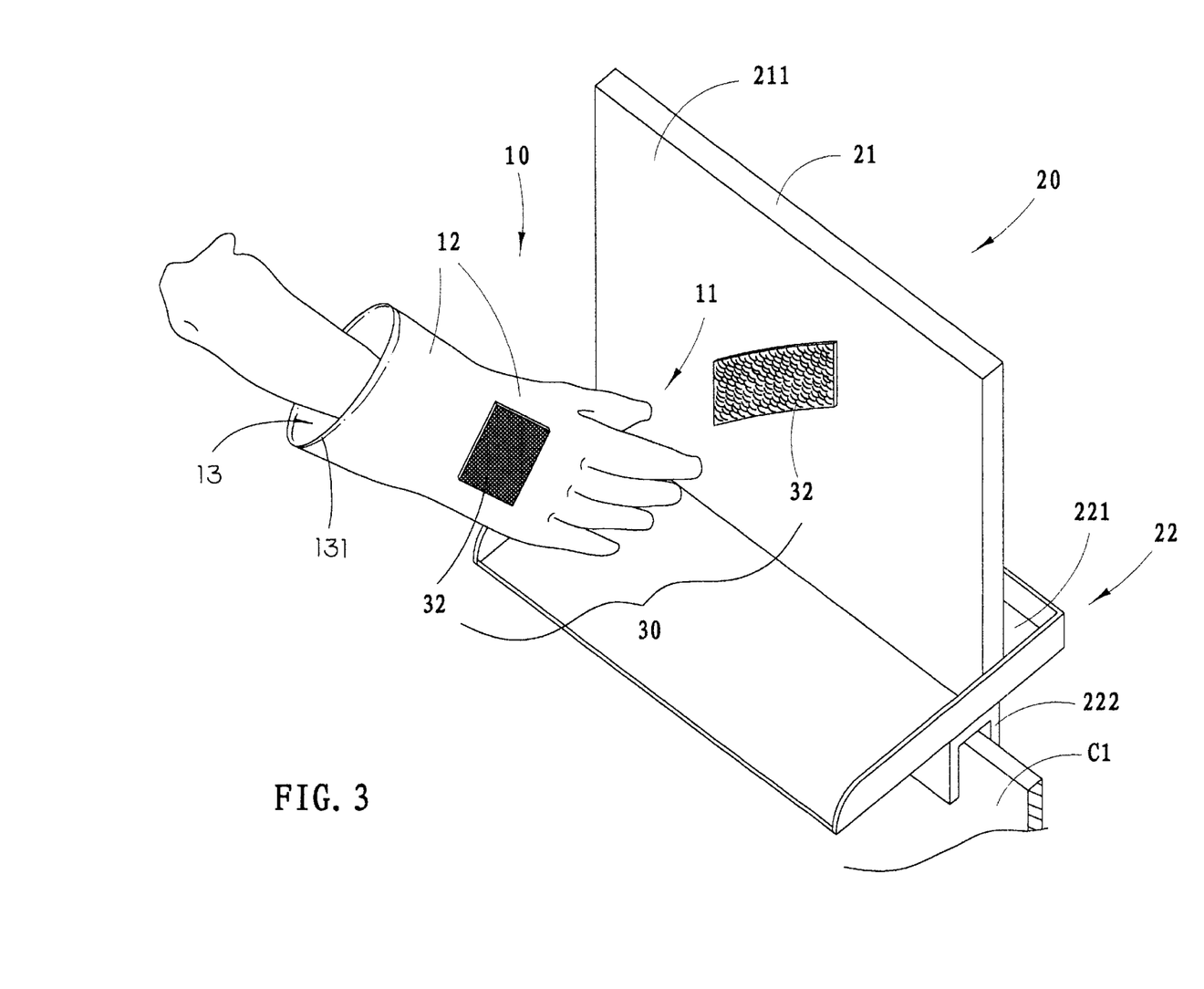
FIG. 3 is a perspective view of a glove donning and doffing arrangement according to a first preferred embodiment of the present invention.

Referring to FIGS. 2 and 3 of the drawings, a glove donning and doffing arrangement according to a preferred embodiment of the present invention is illustrated, which comprises at least a glove 10, a glove station 20 for supporting the glove 10 in a hand-down position, and an attaching means 30 for detachably mounting the glove 10 to the glove station 20 in a hand-down position.

According to the first preferred embodiment, the glove 10 is the specific kind used in chemical industries, which is made of durable material for protecting a wearer from direct skin contacting with chemicals. An exterior surface of the glove 10 has an operating area 11 and a non-operating area 12, wherein the operating area 11 of the glove 10 is defined as the finger portions and the inner side of a hand portion of the glove 10. The non-operating area 12 of the glove 10 is defined by a non-working area of the glove 10 such as an outer side of the hand portion and a wrist portion of the glove 10. In other words, an object is held or grasped within the operating area 11 of the glove 10 and the rest of the glove 10 is the non-operating area 12.

Figure 1:
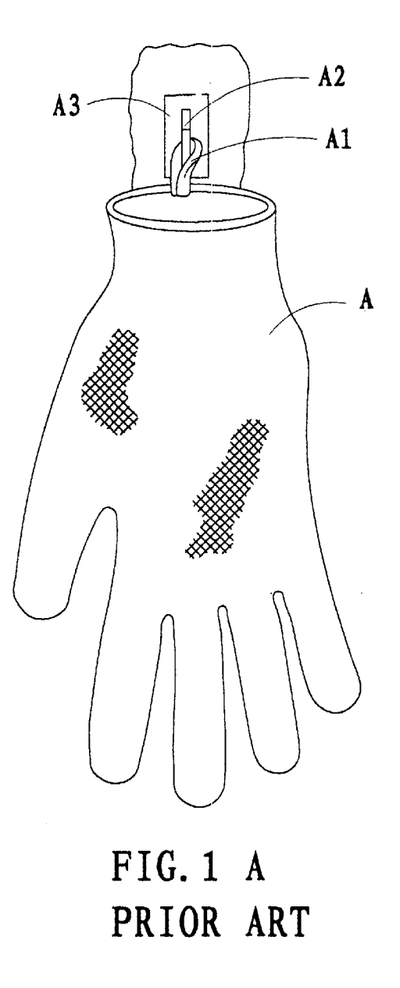
FIGS. 1A and 1B are perspective views of conventional glove stands.
Figure 4:
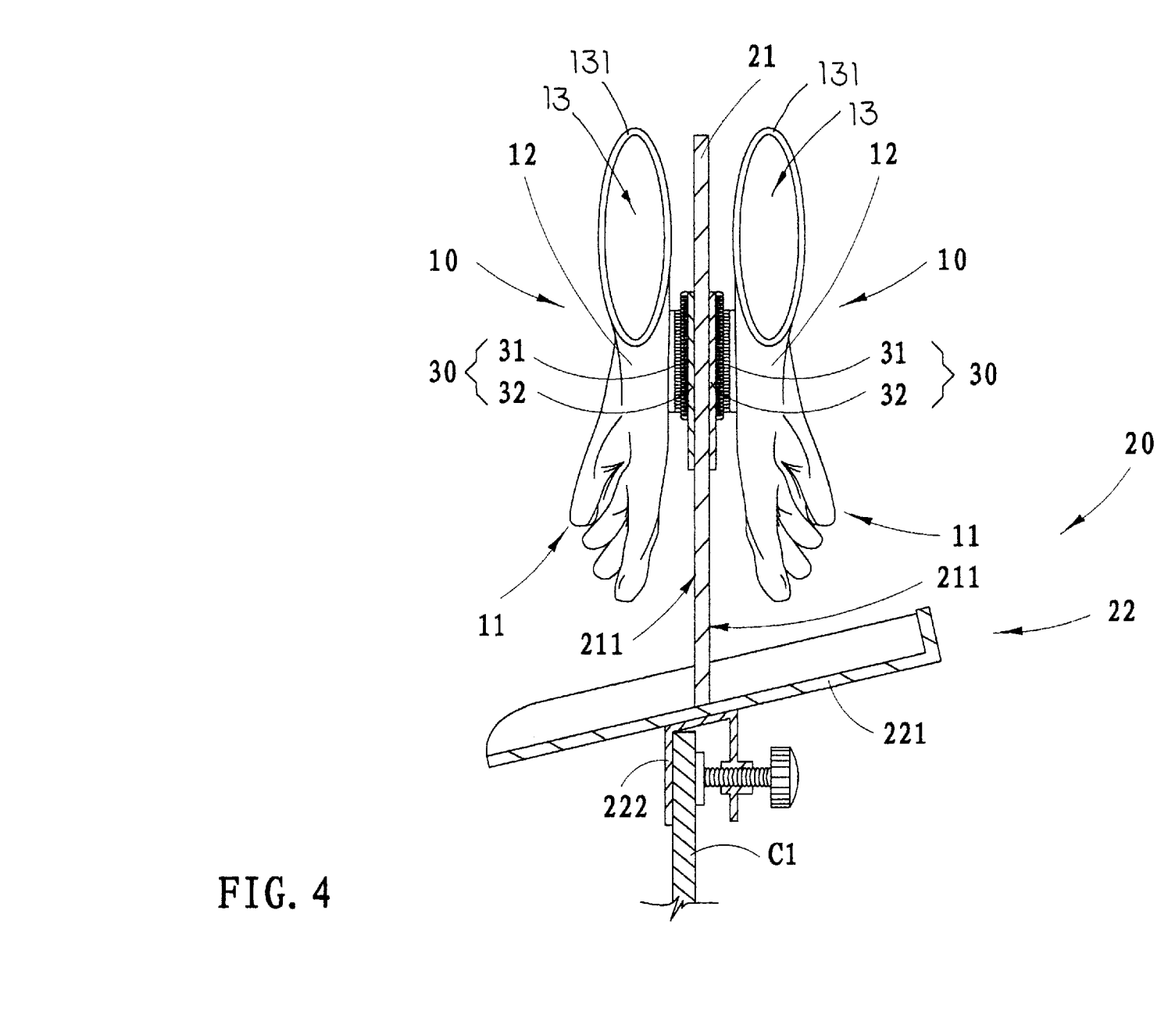
FIG. 4 is a sectional side view of the glove donning and doffing arrangement according to the above first preferred embodiment of the present invention.

As shown in FIGS. 3 and 4, the glove station 20 comprises a vertical supporting panel 21 for supporting the glove 10 on a vertical supporting surface 211 of the supporting panel 21, wherein the supporting panel 21 is adapted for securely mounting on a supporting frame 22. According to the preferred embodiment, the supporting frame 22 comprises a base 221, which is a receiving tray transversally affixed to a bottom of the supporting panel 21 to form the inverted "T" shaped portable glove station 20 and a mounter 222 adapted for firmly mounting the base 221 to a top edge of the washing sink C1 of a chemical wash table C (as shown in FIG. 1). According to the first preferred embodiment, the base 221 is designed to inclinedly affixed on the mounter 222 so that the chemicals dropped from the glove 10 detachably attached to the supporting panel 21 will be collected by the base 221 and guided back into the wash table C.

Alternatively, the base 222 can be a horizontal base without the mounter 222, so that wearer is able to place the glove station 20 in any desired location for supporting the glove 10 conveniently. Alternatively, the supporting panel 21 can also be substantially mounted on a table or a wall, i.e. the supporting frame 22, by means bolt and nut connection.

The attaching means 30 comprises at least a first attaching element 31 provided on the non-operating area 12 of the glove 10 and at least a second attaching element 32 provided on the supporting surface 211 of the supporting panel 21 of the glove station 20. Therefore, the glove 10 is adapted to detachably hold in position on the glove station 20 by attaching the second attaching element 32 to the first attaching element 31 in such a manner the wearer is capable of attaching the glove 10 on the glove station 20 with hands free (another hand) while wearing the glove 10. Preferably, the first and second attaching elements 31, 32 of the attaching means 30 are a set of hook and loop fasteners so as to provide a quick and ease of attachment between the glove 10 and the glove station 20.

According to the first preferred embodiment, two second attaching elements 32 are preferred to be inclinedly affixed to the two supporting surfaces 211 provided on two opposing sides of the supporting panel 21. Accordingly, the glove 10 is adapted to be detachable attached to the glove station 20 in a hand-down position where the wearer's hands are in naturally bending down manner, so that the pair of gloves 10 are adapted for easily donning and doffing the wearer's hand when the gloves 10 are attached on the glove station 20 without skin contacting with the exterior surfaces of the gloves 10.

As shown in FIG. 4, for doffing the glove 10, the wearer naturally hang down his or her hands and then simply attach the non-operating area 12, i.e. the outer side, of his or her right glove 10 to the left side supporting surface 211 of the glove station 20 by attaching the first attaching element 31 provided on the non-operating area 12 to the second attaching element 32 provided on the supporting surface 211. Also, the wearer's left glove 10 can be attached to the right side supporting surface 211 of the glove station 20 by attaching the first attaching element 31 provided on the non-operating area 12 to the second attaching element 32 provided on the supporting surface 211. As shown in FIG. 4, after the gloves 10 are attached and supported on the glove station 20, the wearer's both hands are able to pull out from the glove 10 without any skin contacting with the exterior surface of the gloves 10.

For donning the gloves 10, the wearer should first insert his or her both hands into the two gloves 10 attached on the glove station 20 respectively and then detaches the gloves 10 from the glove station 20 by separating the first attaching elements 31 with the second attaching elements 32. So, based on the entire donning and doffing process of the gloves 10, the wearer does not need to touch any exterior surface of the glove 10 so as to prevent the wearer from being polluted or infected by any chemicals strained on the glove 10.

Figure 5:
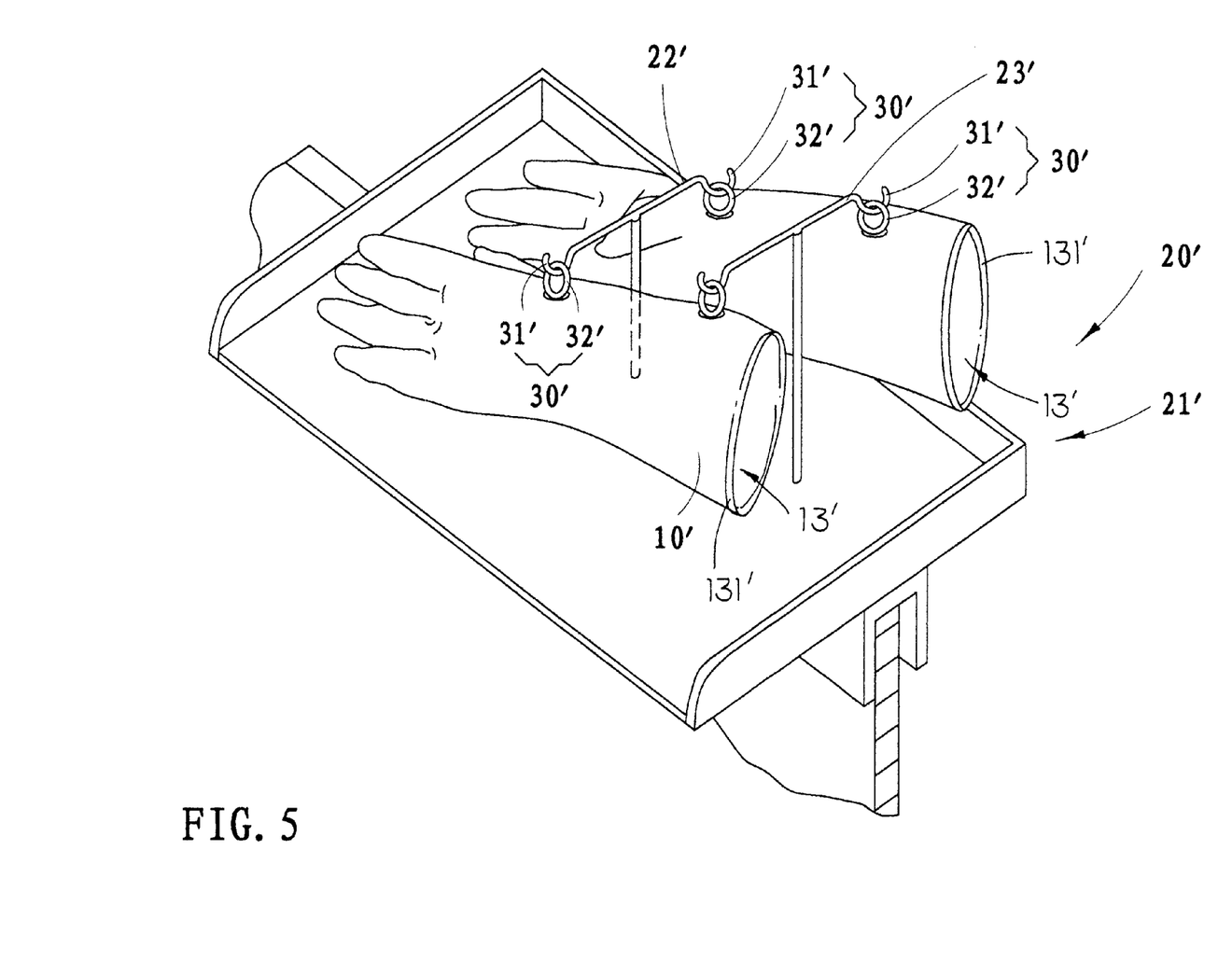
FIG. 5 is a perspective view of a glove donning and doffing arrangement according to a second preferred embodiment of the present invention.
Figure 6:
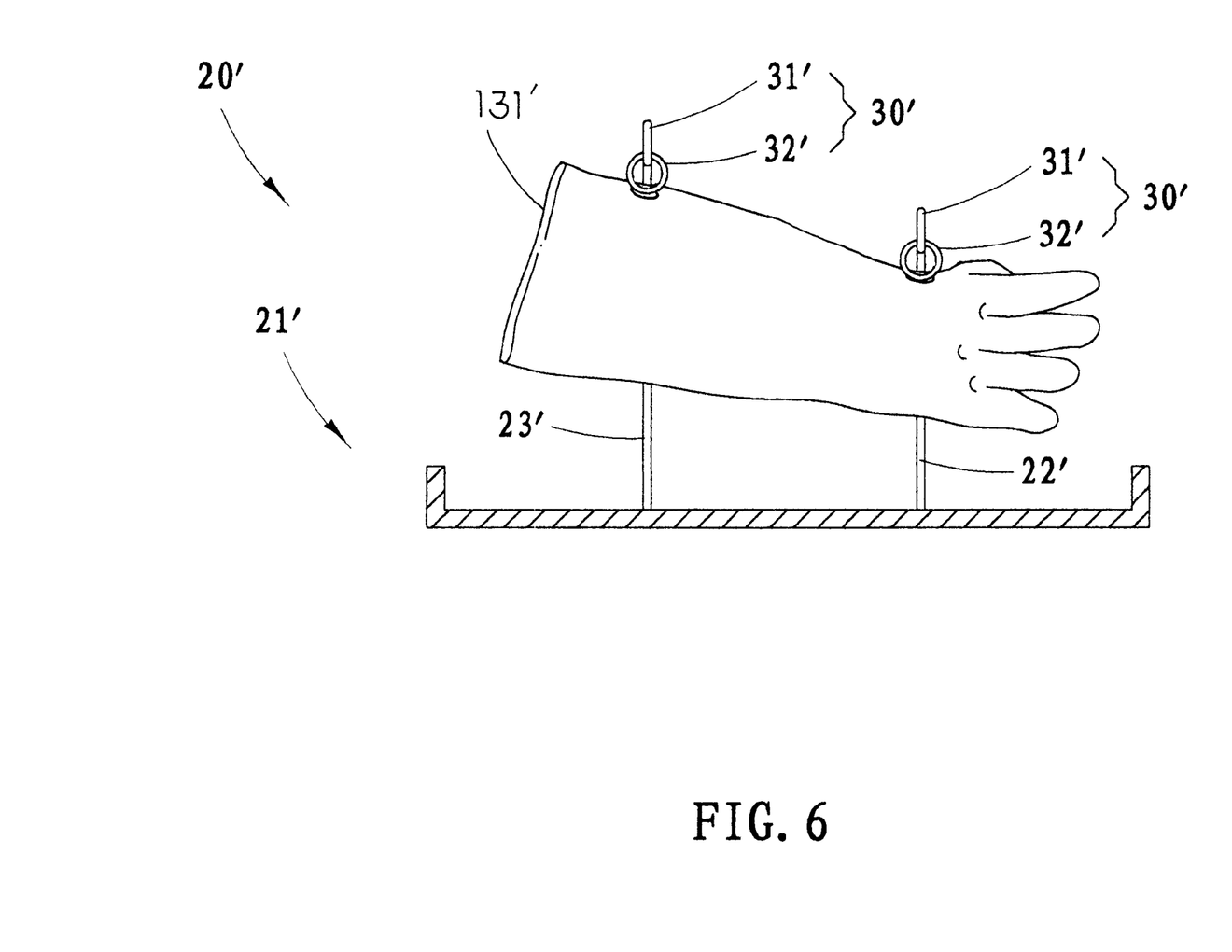
FIG. 6 is a side view of the glove donning and doffing arrangement having the glove supported in a hand-down position according to the above second preferred embodiment of the present invention.

Referring to FIGS. 5 and 6, a glove donning and doffing arrangement according to a second preferred embodiment is illustrated, wherein the second embodiment basically is an alternative mode of the first embodiment that is adapted to support the glove 10' by the glove station 20' in the hand-down position without skin contacting with the exterior surface of the glove 10'.

As shown in FIG. 5, the glove station 20' comprises a supporting frame 21', which can be constructed like the supporting frame 21 of the above first embodiment as shown in FIGS. 3 and 4, and a pair of parallel front and rear supporting arms 22', 23', each having a T-shaped structure, upwardly extended from the supporting frame 21, wherein the front supporting arm 22' is constructed lower than the rear supporting arm 23' with respect to the supporting frame 21', so that the front and rear supporting arms 22', 23' are positioned in a frontwardly inclined manner. As it is mentioned above, the supporting frame 21' can be a pair of vertical posts as shown in FIG. 5 or a wall, so as to substantially support the front and rear supporting arm 22', 23' thereon.

The attaching means 30' comprises two pairs of hook members 31' and two pairs of mounting rings 32'. In which a first pair of the hook members 31 ' provided at two lateral top ends of the front supporting arm 22' and a second pair of the hook members 31 ' provided at two lateral top ends of the rear supporting arms 22', 23'. Each pair of the mounting rings 32' is spacedly and respectively affixed to a frontward portion and a rearward portion of a top edge of the non-operating area 12' of the respective glove 10' in such a manner that the glove 10' is adapted to detachably supported by the glove station 20' by hooking the two mounting rings 32' on the hook members 31' respectively.

Since the front and rear supporting arms 21', 22' of the glove station 20' are in frontward inclined manner, when the glove 10' is supported in a hand-down position on the glove station 20', as shown in FIG. 6.

Figure 7:
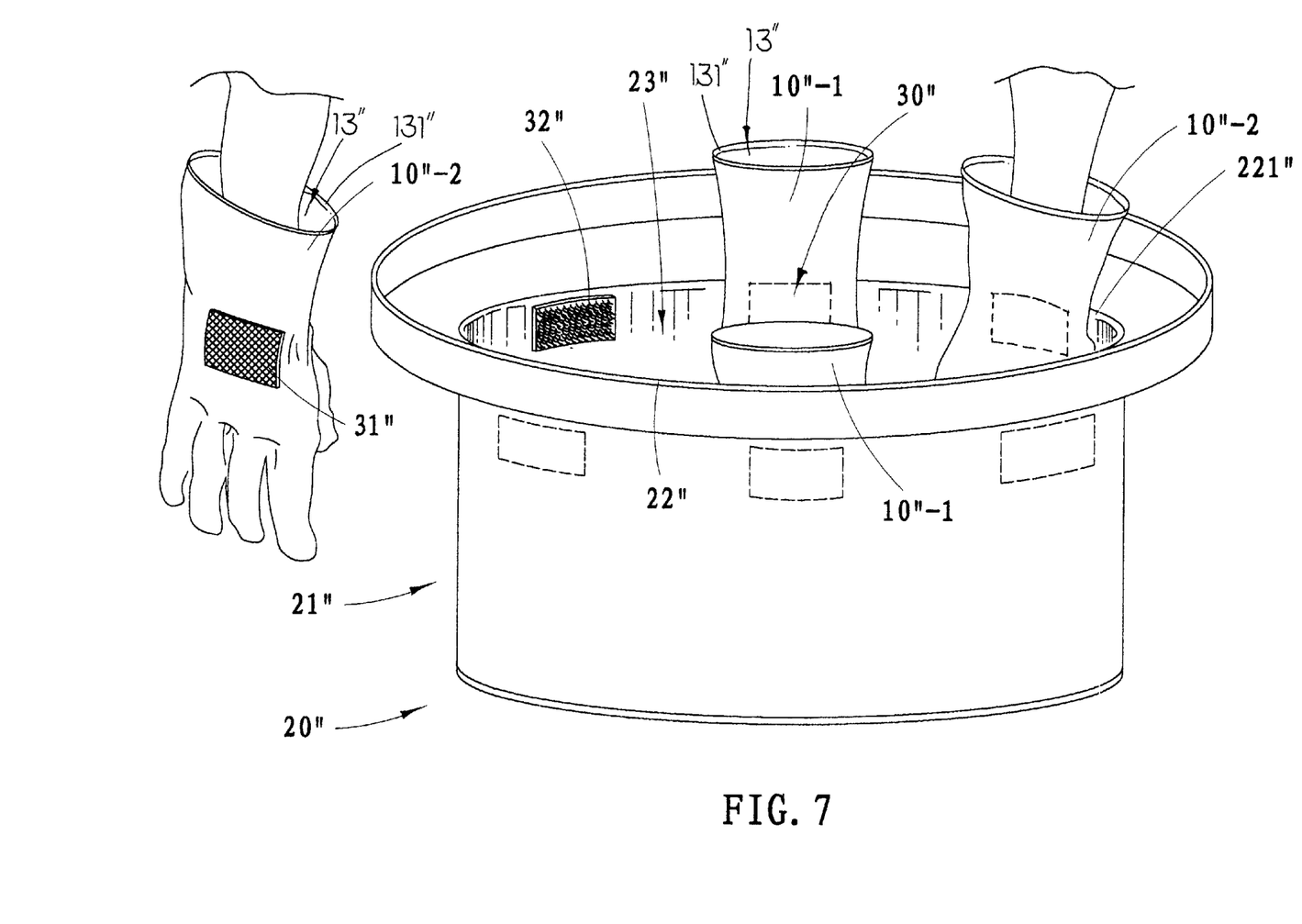
FIG. 7 is a perspective view of a glove donning and doffing arrangement according to a third preferred embodiment of the present invention.

Referring to FIG. 7, a third embodiment of the present invention illustrates an alternative mode of the glove station 20, 20' of the above first and second embodiment, wherein the glove station 20" is adapted for supporting more than a pair of gloves 10" in the hand-down position.

As shown in FIG. 7, the glove station 20" comprises a container body 21" having a supporting wall 22" integrally and upwardly extended therefrom wherein a collecting chamber 23" is defined within the supporting wall 22".

The attaching means 30" comprises a plurality of first attaching elements 31" affixed on the non-operating area 12" of the glove 10" and a plurality of second attaching elements 32" spacedly affixed on an inner surface 221" of the supporting wall 22" of the glove station 20" in such a manner that each of the gloves 10" can be securely attached on the inner surface 221" of the supporting wall 22" of the glove station 20" by attaching the first attaching element 31" on the glove 10" to the second attaching element 32" of the glove station 20".

As shown in FIG. 7, two pairs of gloves 10"-1, 10"-2 are supported by the glove station 20" in the hand-down position, wherein each pair of the gloves 10"-1 or 10"-2 is preferred to be supported to two opposing sides of the glove station 20" while the pairs of second attaching elements 32" are provided spacedly on the inner surface 221" of the supporting wall 22" respectively with a predetermined distance apart from each other. Since the two second attaching elements 32" are mounted apart from each other, the wearer dons and doffs his or her pair of gloves 10" naturally and easily.

Accordingly, for doffing the glove 10", the wearer naturally hangs down his or her hands within the collecting chamber 23" and then simple attaches the pair gloves 10" on the inner surface 221" of the supporting wall 22" of the glove station 20" in the hand-down position. Thus, the chemicals on the glove 10" is received and collected within the collecting chamber 23" when the glove 10" is held by the glove station 20" for cleaning up and further treatment easily.

It is worth to mention that when more than one pair of gloves 10" are supported on the glove station 20", each pair of gloves 10" should have different colors or marks for the wearer to distinguish, so as to avoid any confusion for the wearer.

Furthermore, the glove 10, 10' or 10" used in the above first, second and third embodiment further comprises a loop shaped enforcing wire 131, 131', 131" mounted around a glove opening 13, 13', 13" of the glove 10, 10', 10" so as to facilitate the wearer to insert his or her hand therethrough.

In view of above, the glove donning and doffing arrangement of the present invention can substantially provide the following advantages in comparison with the conventional glove stand:

(1) The chemical work gloves, metal work gloves, auto mechanic gloves, and gardening gloves are all suitable to employ the glove donning and doffing arrangement of the present invention. It enhances the donning and doffing operation of the gloves. Since the gloves are supported on the glove station in the hand-down position that the wearer's hands are in naturally bending manner, the wear is able to wear and remove the gloves easily without skin contacting with the exterior of the gloves so as to prevent the wearer's hands be polluted by the chemicals, stains, grease, or dirt on the gloves.

(2) When the gloves are attached on the glove station in the hand-down position, due to the gravity, the chemicals, stains, grease, or dirt on the gloves will automatically drop down therefrom. Thus, the operating area of the gloves is entirely exposed to the surroundings so as to speed up the drying process of the gloves.

(3) The glove station is adapted for incorporating with any conventional glove wherein simply provides a second attaching element on the conventional glove will achieve the same function as mentioned above. So, any kind of gloves, such as sports gloves, can be used without altering the original structure so as to minimize the manufacturing cost of the gloves incorporating with the glove station.

What is claimed is:

1. A glove donning and doffing arrangement, comprising:
   at least a glove;
   a glove station for supporting said glove thereon in a hand-down position; and
   an attaching means for detachably mounting said glove on said glove station in said hand-down position, wherein said attaching means comprises at least a first attaching element provided on a non-operating area of said glove and at least a second attaching element provided on said glove station, wherein said first and second attaching elements are a set of hook and loop fasteners and said glove is adapted to detachably support on said glove station by attaching said hook fastener with said loop fastener;
   whereby in said hand-down position, a wearer is capable of donning and doffing said glove with said wearer's hand in a naturally hanging down manner.

2. A glove donning and doffing arrangement, comprising:
   at least a glove;
   a glove station for supporting said glove thereon in a hand-down position, said glove station comprises a vertical supporting panel for supporting said glove on a vertical supporting surface of said supporting panel; and
   an attaching means for detachably mounting said glove on said glove station in said hand-down position, wherein said attaching means comprises at least a first attaching element provided on a non-operating area of said glove and at least a second attaching element provided on said glove station, wherein said first and second attaching elements are a set of hook and loop fasteners and said glove is adapted to detachably support on said glove station by attaching said hook fastener with said loop fastener;
   whereby in said hand-down position, a wearer is capable of donning and doffing said glove with said wearer's hand in a naturally hanging down manner.

3. A glove donning and doffing arrangement, comprising:
   at least a glove;
   a glove station for supporting said glove thereon in a hand-down position, said glove station comprises a vertical supporting panel for supporting said glove on a vertical supporting surface of said supporting panel; and
   an attaching means for detachably mounting said glove on said glove station in said hand-down position, wherein said attaching means comprises at least a first attaching element provided on a non-operating area of said glove and at least a second attaching element provided on said glove station, wherein said first attaching element is provided on an outer side of a hand portion of said glove and said second attaching element is provided on said vertical supporting surface of said supporting panel of said glove station, wherein said first and second attaching elements are a set of hook and loop fasteners and said glove is adapted to detachably support on said glove station by attaching said hook fastener with said loop fastener;
   whereby in said hand-down position, a wearer is capable of donning and doffing said glove with said wearer's hand in a naturally hanging down manner.

4. A glove donning and doffing arrangement, comprising:
   at least a glove;
   a glove station for supporting said glove thereon in a hand-down position, wherein said glove station comprises a supporting frame and a pair of parallel front and rear supporting arms upwardly extended from said supporting frame, wherein said front supporting arm has a height, with respect to said supporting frame, lower than said rear supporting arm so as to position said front and rear supporting arms in a frontward inclined manner; and an attaching means for detachably mounting said glove on said glove station in said hand-down position;

whereby in said hand-down position, a wearer is capable of donning and doffing said glove with said wearer's hand in a naturally hanging down manner.

5. A glove donning and doffing arrangement, comprising:

at least a glove;

a glove station for supporting said glove thereon in a hand-down position, wherein said glove station comprises a supporting frame and a pair of parallel front and rear supporting arms upwardly extended from said supporting frame, wherein said front supporting arm has a height, with respect to said supporting frame, lower than said rear supporting arm so as to position said front and rear supporting arms in a frontward inclined manner; and an attaching means for detachably mounting said glove on said glove station in said hand-down position, wherein said attaching means comprises at least a first attaching element provided on a non-operating area of said glove and at least a second attaching element provided on said glove station, wherein said glove is adapted to detachably support on said glove station by attaching said first attaching element to said second attaching element;

whereby in said hand-down position, a wearer is capable of donning and doffing said glove with said wearer's hand in a naturally hanging down manner.

6. A glove donning and doffing arrangement, as recited in claim 4, wherein each of said front and rear supporting arms has a T-shaped structure.

7. A glove donning and doffing arrangement, as recited in claim 5, wherein each of said front and rear supporting arms has a T-shaped structure.

8. A glove donning and doffing arrangement, as recited in claim 5, further comprising another glove to form a pair of gloves and each said attaching means comprising a pair of second attaching elements which are hook members and a pair of first attaching elements which are mounting rings, wherein two of said hook members are provided at two lateral top ends of said front supporting arm and another two of said hook members provided at two lateral top ends of said rear supporting arms, wherein each said pair of said mounting rings is spacedly and respectively affixed to a frontward portion and a rearward portion of a top edge of said non-operating area of the respective glove in such a manner that each of said gloves is adapted to be detachably supported by the glove station by hooking the two mounting rings on the hook members respectively.

9. A glove donning and doffing arrangement, as recited in claim 7, further comprising another glove to form a pair of gloves and each said attaching means comprising a pair of second attaching elements which are hook members and a pair of first attaching elements which are mounting rings, wherein two of said hook members are provided at two lateral top ends of said front supporting arm and another two of said hook members provided at two lateral top ends of said rear supporting arms, wherein each said pair of said mounting rings is spacedly and respectively affixed to a frontward portion and a rearward portion of a top edge of said non-operating area of the respective glove in such a manner that each of said gloves is adapted to be detachably supported by the glove station by hooking the two mounting rings on the hook members respectively.

10. A glove donning and doffing arrangement, comprising:

a plurality of gloves;

a glove station for supporting said gloves thereon in a hand-down position, wherein said glove station comprises a container body having a supporting wall integrally and upwardly extended therefrom wherein a collecting chamber is defined within said supporting wall; and a plurality of attaching means for detachably mounting said gloves on said glove station in said hand-down position, wherein each of said attaching means comprises at least a first attaching element provided on a non-operating area of said respective glove and at least a second attaching element provided on said glove station, wherein each of said gloves is adapted to detachably support on said glove station by attaching said first attaching element to said second attaching element;

whereby in said hand-down position, a wearer is capable of donning and doffing said glove with said wearer's hand in a naturally hanging down manner.

11. A glove donning and doffing arrangement, as recited in claim 10, wherein each of said gloves which has said first attaching element thereof is affixed on said non-operating area of said glove and said respective second attaching element on an inner surface of said supporting wall of said glove station, wherein said second attaching elements of said gloves are spacedly provided on said inner surface of said supporting wall in such a manner that said gloves are capable of securely attaching on said inner surface of said supporting wall of said glove station in said hand-down position by attaching said first attaching elements on said gloves to said second attaching elements of said glove station respectively and correspondingly.

12. A glove donning and doffing arrangement, as recited in claim 11, wherein said pairs of said gloves have specific colors respectively to distinguish from each other.

13. A glove donning and doffing arrangement, as recited in claim 9, wherein each of said gloves further comprises a loop shaped enforcing wire mounted around a glove opening of said glove so as to support said glove opening.

14. A glove donning and doffing arrangement, as recited in claim 11, wherein each of said gloves further comprises a loop shaped enforcing wire mounted around a glove opening of said glove so as to support said glove opening.

* * * * *